United States Patent [19]

Oka et al.

[11] Patent Number: 5,256,548
[45] Date of Patent: Oct. 26, 1993

[54] ANTIVIRAL ANTIBIOTIC BU-4344V

[75] Inventors: Masahisa Oka, Yokahama; Koji Tomita, Tokyo; Osamu Tenmyo, Yokohama; Nobuaki Naruse, Chiba, all of Japan

[73] Assignee: Bristol-Myers Squibb Company, New York, N.Y.

[21] Appl. No.: 874,775

[22] Filed: Apr. 27, 1992

Related U.S. Application Data

[62] Division of Ser. No. 616,518, Nov. 21, 1990, Pat. No. 5,140,101.

[51] Int. Cl.$^5$ .................. C12P 21/04; C12R 1/03; C07K 7/54; C12N 1/12
[52] U.S. Cl. .................. 435/71.3; 435/252.1; 435/825
[58] Field of Search ............... 530/317, 321; 435/71.3, 435/825, 252.1

[56] References Cited

U.S. PATENT DOCUMENTS

| | | | |
|---|---|---|---|
| 4,328,211 | 5/1982 | Sugawara et al. | 435/169 |
| 4,399,067 | 8/1983 | DeBono | 530/317 |
| 4,882,419 | 11/1989 | Malabarba et al. | 530/317 |
| 4,946,941 | 8/1990 | Kondo et al. | 530/317 |

FOREIGN PATENT DOCUMENTS 0316873  8/1989  European Pat. Off. ............ 530/317

OTHER PUBLICATIONS

"ATCC Catalogue of Bacteria & Bacteriophages" 17th Ed. 1989 pp. 7-8 Actinomadura, Primary Examiner—Herbert J. Lilling
Attorney, Agent, or Firm—Aldo A. Algieri

[57] ABSTRACT

There is provided a new antiviral antibiotic designated herein as BU-4344V which is produced by fermentation of a BU-4344V-producing strain of a new microorganism, Actinomadura parvosata subsp. kistnae ATCC No. 55076. Antibiotic BU-4344V is recovered and purified from the fermentation broth by use of extraction, chromatography, and crystallization techniques. BU-4344V has been found to have some antibacterial activity and inhibits the growth of viruses, including influenza virus type A.

2 Claims, 4 Drawing Sheets

ANTIVIRAL ANTIBIOTIC BU-4344V

CROSS-REFERENCE TO RELATED APPLICATION

This is a divisional of copending application U.S. Ser. No. 07/616,518, filed Nov. 21, 1990, now U.S. Pat. No. 5,140,101.

SUMMARY OF THE INVENTION

This invention relates to a new antiviral antibiotic designated herein as BU-4344V, to its preparation by fermentation of a new microorganism, *Actinomadura parvosata subsp. kistnae* ATCC No. 55076, or a mutant thereof, in an aqueous fermentation culture nutrient medium containing assimilable sources of nitrogen and carbon under submerged aerobic conditions until a substantial amount of the antiviral antibiotic designated BU-4344V is produced by the organism in the fermentation culture nutrient medium, and to its recovery from the fermentation medium. This invention also relates to the pharmaceutical compositions containing the new antiviral antibiotic and methods for using said antiviral antibiotic as an antimicrobial and antiviral agent.

DETAILED DESCRIPTION OF THE INVENTION

Figure 1:
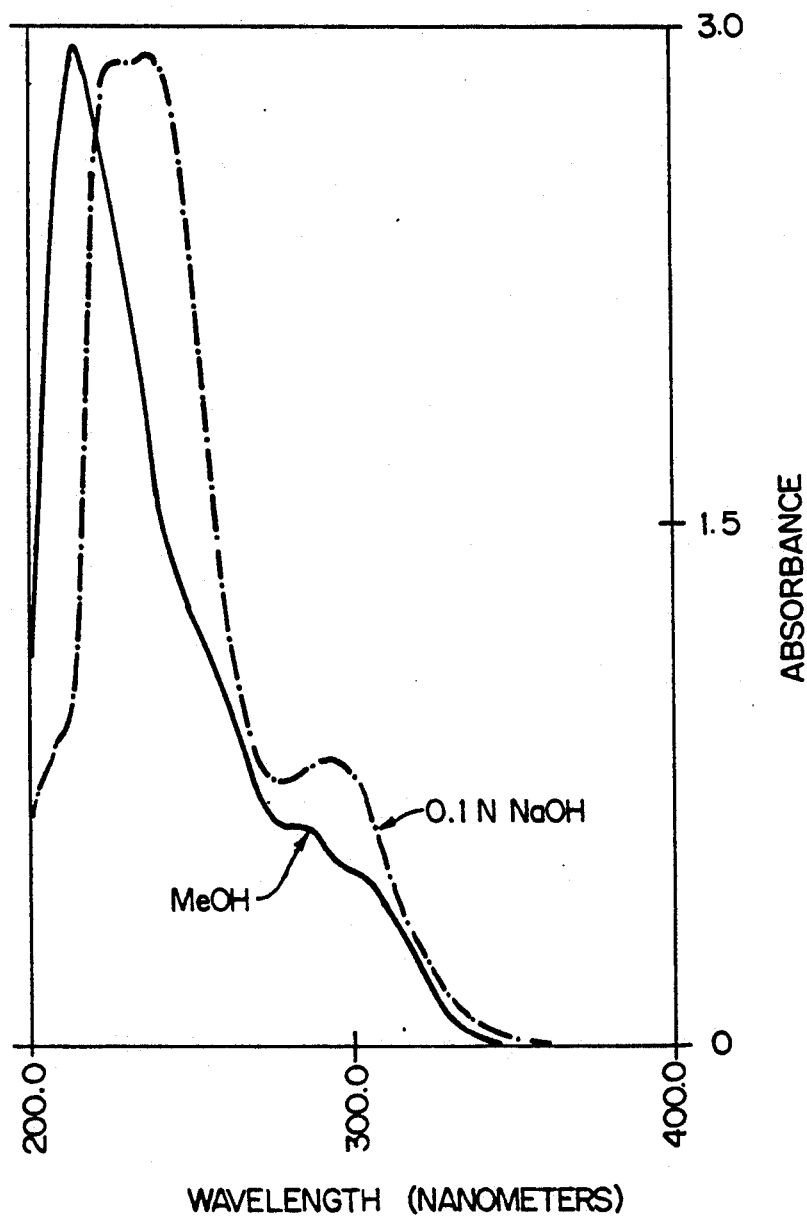
FIG. 1 shows the ultraviolet (UV) absorption spectrum of BU-4344V at a concentration of 50 μg/ml in methanol and in 0.1N sodium hydroxide.

The present invention relates to a new antiviral antibiotic, designated BU-4344V, which is produced by fermenting a BU-4344V-producing strain of *Actinomadura parvosata*, preferably the strain *Actinomadura parvosata* subsp. *kistnae*, and most preferably the strain *Actinomadura parvosata* subsp. *kistnae* ATCC No. 55076.

In another aspect, this invention is a pharmaceutical composition of BU-4344V

In yet another aspect, this invention is a process for producing the novel antiviral antibiotic BU-4344V.

In still another aspect, this invention provides a method for inhibiting the growth of viruses comprising contacting such viruses with a growth-inhibitory effective amount of the novel antiviral antibiotic, BU-4344V In still yet another aspect, this invention provides a novel microorganism *Actinomadura parvosata* subsp. *kistnae* ATCC No. 55076.

The novel antiviral antibiotic BU-4344V is obtained by fermentation of a new microorganism classified as a species of the genus Actinomadura, accumulating BU-4344V produced by said microorganism and collecting the antiviral antibiotic BU-4344V from the culture broth. A preferred BU-4344V-producing microorganism is the Actinomadura sp. Strain No. S382-8 isolated from a soil sample collected near the Kistna River in Andhra Pradesh State, India. Based on the taxonomic descriptions of this genus and the comparative studies to the relevant species, Strain No. S382-8 was classified as *Actinomadura parvosata* subsp. *kistnae* subsp. nov. and was deposited in the American Type Culture Collection, Rockville, Md., under the accession number ATCC 55076. The permanency of the deposit of this culture at the American Type Culture Collection at Rockville, Md., and ready accessibility thereto by the public are afforded throughout the effective life of the patent in the event the patent is granted. Access to the culture is available during pendency of the application under 37 C.F.R. 1.14 and 35 U.S.C. 112. All restrictions on the availability to the public of the culture ATCC No. 55076 deposited will be irrevocably removed upon granting of the patent.

THE MICROORGANISM

The following is a general description of the preferred microorganism producing the ANITIVIRAL ANTIBIOTIC BU-4344V.

Morphology

The substrate mycelium of Strain No. S382-8 is well-branched and non-fragmentary (0.5 μm in diameter). Aerial mycelium is poorly formed on limited media and bears monopodially chains of spore The spore chains are short (10 to 20 spores per chain), mostly sessile and hook or tightly closed spiral at tip Some tightly closed spirals are observed as a pseudosporangium. The spores are spherical or oblong (0.7–0.9×0.8–1.5 μm), non-motile, and have a smooth surface.

Cultural Characteristics

Strain No. S382-8 grows well in nutritionally rich organic media and poorly in chemically defined media. The color of substrate mycelia is colorless, brownish pink to deep red. The aerial mycelium, if formed, is white Melanoid and other distinct diffusible pigments are not formed. The cultural characteristics of Strain No. S382-8 are shown in Table 1.

Physiological Characteristics

Strain No. S382-8 shows growth between 22° C. and 45° C. The tolerance to NaCl is seen at 3% but not at 4%. It is sensitive to lysozyme. The physiological characteristics of Strain No. S382-8 are shown in Tables 2 and 3. Most of the diagnostic sugars are utilized for growth.

The aforementioned cultural and physiological characteristics of Strain No. S382-8 were examined by the methods described by E. B. Shirling, et al., in *Int. J. Syst. Bacteriol.* 16, 313–340 (1966) and R. E. Gordon, et al. in *J. Gen. Microbiol.* 109, 69–78 (1978).

Cell Chemistry

Whole cell hydrolysate contains meso-diaminopimelic acid, ribose, madurose, mannose, galactose, and glucose. Therefore, Strain No. S382-8 belongs to cell wall Type III and sugar pattern B.

The phospholipids contain phosphatidylethanolamine (PE), phosphatidylglycerol (PG), phosphatidylinositol (PI), phosphatidylinositol mannoside (PIM), and unknown glucosamine-containing phospholipids (GluNUs) and, hence, belong to Type P-IV. The major menaquinone is MK-9 ($H_4$). The whole cell amino acids and sugars, the phospholipids, and the menaquinone were analyzed by the methods of M. P. Lechevalier in *J. Lab. Clin. Med.*, 71, 934–944 (1968), M. P. Lechevalier, et al., in *Biochem. Syst. Ecol.*, 5, 249–260 (1977), and M. D. Collins, et al., in *J. Gen. Microbiol.*, 100, 221–230 (1977), respectively

TABLE 1

Cultural Characteristics of Strain No. S382-8*

| Medium | Growth | Aerial Mycelium | Substrate Mycelium | Diffusible Pigment |
|---|---|---|---|---|
| Sucrose-nitrate agar (Czapek-Dox agar) | Poor | Moderate; white | Colorless to brownish pink (33)** | None |
| Tryptone-yeast extract broth (ISP No. 1) | Moderate, not turbid | None | Colorless | None |
| Yeast extract-malt extract agar (ISP No. 2) | Good | None or scant; whitish | Very deep red (14) | None |
| Oatmeal agar (ISP No. 3) | Moderate | Scant; whitish | Grayish red (19) | Grayish pink (8) |
| Inorganic salts-starch agar (ISP No. 4) | Poor | None | Deep yellowish brown (75) | None |
| Glycerol-asparagine agar (ISP No. 5) | Poor | None | Brownish pink (33) | None |
| Peptone-yeast extract-iron agar (ISP No. 6) | Poor | None | Moderate reddish brown (43) | None |
| Tyrosine agar (ISP No. 7) | Poor | None or scant; white | Brownish pink (33) | None |
| Glucose-asparagine agar | Poor | None | Colorless | None |
| Nutrient agar | Poor | None | Very deep red (14) | None |
| Bennett's agar | Moderate | None | Dark red (16) | None |

*Observed after incubation at 28° C. for 3 weeks.
**Color name and number in parenthesis follow the color standards in ISCC-NBS color name charts.

TABLE 2

Physiological Characteristics of Strain No. S382-8

| Hydrolysis of: | |
|---|---|
| Gelatin | + (Slow) |
| Starch | Trace |
| Milk Coagulation | − |
| Peptonization | − |
| Production of: | |
| Nitrate Reductase | + |
| Tyrosinase | − |
| Tolerance to: | |
| Lysozyme, 0.01% | − |
| NaCl, 3% | + |
| NaCl, 4% | − |
| pH, 5.3–10 | + |
| Temperature: | |
| Growth Range | 22° C.–45° C. |
| Optimal Growth | 37° C.–42° C. |
| No Growth | 19° C. and 48° C. |
| Carbohydrate Utilization of:* | |
| Glycerol | + |
| D-Arabinose | + |
| L-Arabinose | + |
| D-Xylose | + |
| D-Ribose | + |
| L-Rhamnose | + |
| D-Glucose | + |
| D-Galactose | + |
| D-Fructose | + |
| D-Mannose | + |
| L-Sorbose | − |
| Sucrose | + |
| Lactose | + |
| Cellobiose | + |

TABLE 2-continued

Physiological Characteristics of Strain No. S382-8

| Melibiose | + |
|---|---|
| Trehalose | + |
| Raffinose | + |
| D-Melezitose | − |
| Soluble Starch | + |
| Cellulose | − |
| Dulcitol | − |
| Inositol | +$^{w**}$ |
| D-Mannitol | +$^{w}$ |
| D-Sorbitol | + |
| Salicin | + |

Abbreviation:
+, Positive Characteristic;
−, Negative Characteristic
*Basal Medium: Pridham and Gottlieb's inorganic salts medium (= ISP Medium No. 9).
*Abbreviation:
+, Positive Utilization;
−, Negative Utilization
**+$^{w}$, Weakly Positive

TABLE 3

Physiological Characteristics of Strain No. S382-8

| Decomposition of: | |
|---|---|
| Adenine | − |
| Casein | + |
| Esculin | + |
| Hippuric acid | + |
| Hypoxanthine | + |
| Tyrosine | + |
| Urea | − |
| Xanthine | − |
| Survival at 50° C., 8 h | − |
| Utilization of: | |
| Na-benzoate | − |
| Na-citrate | − |
| Na-mucate | − |
| Na-succinate | + |
| Na-tartrate | − |
| Acid from: | |
| Adonitol | + |
| Arabinose | + |
| Cellobiose | + |
| Erythritol | − |
| Glucose | + |
| Glycerol | + |
| Inositol | + |
| Lactose | + |
| Maltose | + |
| Mannose | + |
| Melezitose | − |
| Melibiose | + |
| Methyl α-glucoside | +$^{w}$ |
| Raffinose | + |
| Rhamnose | + |
| Sorbitol | − |
| Trehalose | + |
| Xylose | + |

Abbreviation:
+, Positive Characteristic;
−, Negative Characteristic

Taxonomic Position

The above-mentioned morphology and cultural, and physiological characteristics, as well as the cell chemistry, indicate that Strain No. S382-8 is placed in the genus Actinomadura. Chemotaxonomically, Actinomadura includes two distinct groups, *A. madurae* group and *A. pusilla* group. Strain No. S382-8 belongs to *A. pusilla* group which has Type P-IV phospholipids and MK-9(H$_4$) as the major menaquinone [*A. madurae* group has Type P-I phospholipids and MK-9(H$_6$) or MK-9(H$_8$) menaquinones]. *A. pusilla* group was, thus, proposed to be separated from Actinomadura as a genus, Nonomuria by M. Goodfellow, et al. [Chemotaxonomy and actinomycete systematics, p. 233-238, in Y. Okami, T. Beppu, and H. Ogawara (ed.), Biology of Actinomycetes '88, 1988, Japan Scientific Societies Press]. According to the criteria of Nonomuria by Goodfellow, et al., the following species should be transferred to Nonomuria: Actinomadura pusilla. A. fastidiosa, A. ferruoinea, A. helvata, A. kijaniata, A. libanotica, A. roseola, A. roseoviolacea, A. rubra. A. salmonea, A spiralis, A. luzonesis [K. Tomita, et al., J. Antibiotics, 33, 1098–1102 (1980); unpublished data], and Actinomadura parvosata: [S. B. Christensen, et al.: J. Antibiotics. 40, 970–990 (1987)].

In spite of the above-mentioned taxonomic status of the present organism for nomenclature, the Nonomuria does not become an approved name by ICSB (the International Committee on Systematic Bacteriology), and Strain No. S382-8 is, thus, retained in the genus Actinomadura.

Strain No. S382-8 forms pink, red, or deep reddish brown pigments in the substrate mycelia. Concerning this pigmentation, Strain No. S382-8 resembles *A. roseola, A. roseoviolacea, A. rubra, A. salmonea* [T. P. Preobrazhenskaya, et al., *The Biology of the Actinomycetes and Related Organisms*, 12, 30–38 (1977)], *A. luzonensis* and *A. parvosata*. According to the descriptions of M. Athalye, et al., in *Int. J. Syst. Bacteriol.*, 35, 86–98 (1985) and K. Tomita, et al., in *J. Antibiotics*, 33, 1098–1102 (1980), the above five species, except for *A. parvosata*, are physiologically differentiated from Strain No. S382-8. In addition, *A. roseola, A. rubra*, and *A. salmonea* have warty spores while Strain No. S382-8 has smooth spores.

Strain No. S382-8 is most similar to *A. parvosata* in the morphology and physiology. However, as shown in Table 4, Strain No. S382-8 is differentiated from *A. parvosata* in some cultural and physiological characteristics. Thus, Strain No. S382-8 is designated *Actinomadura parvosata* subsp. kistnae subsp. nov. and was deposited in the American Type Culture Collection, Rockville, Md., under the accession number ATCC 55076.

TABLE 4

| Differential Characteristics Between Strain No. S382-8 and Actinomadura parvosata SK&F-AAJ-271 | | |
|---|---|---|
| Test | Strain S382-8 | A. parvosata |
| Coproduction of purplish pigment in nutritionally rich organic media, eg., ISP Media Nos. 2 and 3 | — | + |
| Decomposition of: | | |
| Adenine | — | + |
| Urea | — | + |
| Utilization of: | | |
| Citrate | — | + |
| Acid from: | | |
| D-Sorbitol | — | + |

Abbreviation:
+, Positive Characteristic;
—, Negative Characteristic

PREPARATION, ISOLATION, AND PURIFICATION, OF BU-4344V

The process for producing the antiviral antibiotic BU-4344V, according to the present invention, comprises the steps of:

(a) cultivating *Actinomadura parvasata* subsp. kistnae ATCC No. 55076 in an aqueous fermentation culture nutrient medium containing assimilable sources of nitrogen and carbon under submerged aerobic conditions until a substantial amount of BU-4344V is produced in the fermentation culture medium;

(b) separating the mycelium and other undissolved residues from the fermentation culture medium to obtain a supernatant liquid which contains antibiotic activity;

(c) adsorbing the antibiotic component in the supernatant liquid from Step (b) on a Sephadex LH-20 column;

(d) separating the antibiotic by selective gradient elution techniques;

(e) adsorbing the antibiotic component contained in the eluate from Step (d) on a reversed-phase $C_{18}$ silica gel column;

(f) separating the antibiotic component adsorbed to the column in Step (e) by selective gradient elution techniques; and (g) recovering from the eluate from Step (f) the antiviral antibiotic BU-4344V by at least one conventional adsorption technique and crystallization technique.

The assimilable carbon source for use in the aqueous fermentation culture medium may be a carbohydrate such as, for example, glucose, ribose, galactose, fructose, mannose, sucrose, lactose, soluble starch, and glycerol to name a few.

The assimilable nitrogen source for use in the aqueous fermentation culture medium may be any one of such conventionally known sources, including fish meal, soybean meal, corn steep liquor, peptones, meat extract, peanut flour, yeast extract, and ammonium salts to name but a few.

Inorganic salts, such as sodium chloride, potassium chloride, magnesium sulfate, calcium carbonate, phosphates, and the like, may be added if desired In addition, trace elements, such as copper, manganese, iron, zinc, and the like, may be added if desired or they may be supplied as minor or trace impurities of other constituents in the fermentation media.

The incubation temperature may be any temperature at which a BU-4344V-producing strain is able to grow. Preferably, the incubation temperature is about 22°–45° C., more preferably about 25°–35° C., and most preferably about 27°–32° C.

A neutral or nearly neutral initial pH, for example, pH about 6-8, is preferably employed in the fermentation media, and production of the antiviral antibiotic by fermentation is generally carried out for a period of about 2-10 days. Ordinarily, optimum production is achieved in about 4-7 days. For the preparation of relatively small amounts of the antiviral antibiotic, shake flasks and surface culture can be employed whereas for relatively large amounts submerged aerobic culture in sterile fermentation tanks is preferred. When tank fermentation is to be carried out, it is desirable to produce a vegetative inoculum in a nutrient broth by inoculating the broth culture with a spore from the organism and, when a young active vegetative inoculum has been obtained, transferring the inoculum aseptically to the fermentation tank medium. Aeration in tanks and bottles may be provided by forcing sterile air through or onto the surface of the fermentation medium. Further agitation of the medium may be provided by a mechanical impeller and an antifoaming agent such as is conventional in the art, e.g., lard oil may be added as needed.

The production of the antiviral antibiotic BU-4344V in the fermentation medium may be followed readily during the course of the fermentation by the conventional dye-uptake assay method using influenza virus Type A.

After optimum fermentation broth potency has been obtained (as determined by the above-described assay method), the mycelium and undissolved residues are separated from the fermentation broth by conventional means, such as filtration and centrifugation, to obtain a supernatant liquid (or filtrate) which contains antibiotic activity. The component having antibiotic activity can be recovered from the supernatant liquid by employing conventional adsorption techniques.

In one preferred embodiment, the fermentation broth is extracted with an alkanol solvent, preferably n-butanol, and the oil produced after concentration was triturated with water and then extracted with ethyl acetate and n-butanol. The n-butanol extract containing the antibiotic component was concentrated. The resulting powder was dissolved in alkanol, preferably methanol, and applied to a column packed with Sephadex LH-20 resin (Sephadex is a trademark owned by Pharmacia Fine Chemicals Inc.), and the resin is eluted with methanol. The eluate fractions having antibiotic activity are combined and concentrated in vacuo. The resulting amorphous powder is then applied to a column packed with reversed-phase silica gel, corresponding to the content of a PrepPAK-500/$C_{18}$ cartridge column (commercially available from Waters Associates), and the column is then eluted with an aqueous solution containing 30%, 40%, 60%, 80%, and 100% (Volume %) of methanol. The resulting antibiotic activity-containing eluate is concentrated in vacuo to provide a semi-pure solid. This semi-pure solid is then applied to a column packed with silica gel (Merck Kieselgel 60), and the silica gel column is first eluted with 20% methanol-dichloromethane and then with 50% methanol-dichloromethane. Crystallization of a sample obtained from the latter eluate afforded colorless needles of the pure antiviral antibiotic BU-4344V.

PHYSICO-CHEMICAL CHARACTERIZATION OF BU-4344V

The antiviral antibiotic BU-4344V was isolated as colorless needles. It was soluble in dimethyl sulfoxide, methanol, and alkaline water (such as 1N $NH_{40}H$ and 1% aqueous $NaHCO_3$) but insoluble in dichloromethane, n-hexane, and water. It gave positive responses to iodine vapor, sulfuric acid, ferric chloride, and Rydon-Smith test but negative ones to Dragendorff and anthrone-sulfuric acid tests on a silica gel TLC plate. BU-4344V migrated to the anode at pH 8.0 by paper electrophoresis.

Figure 2:
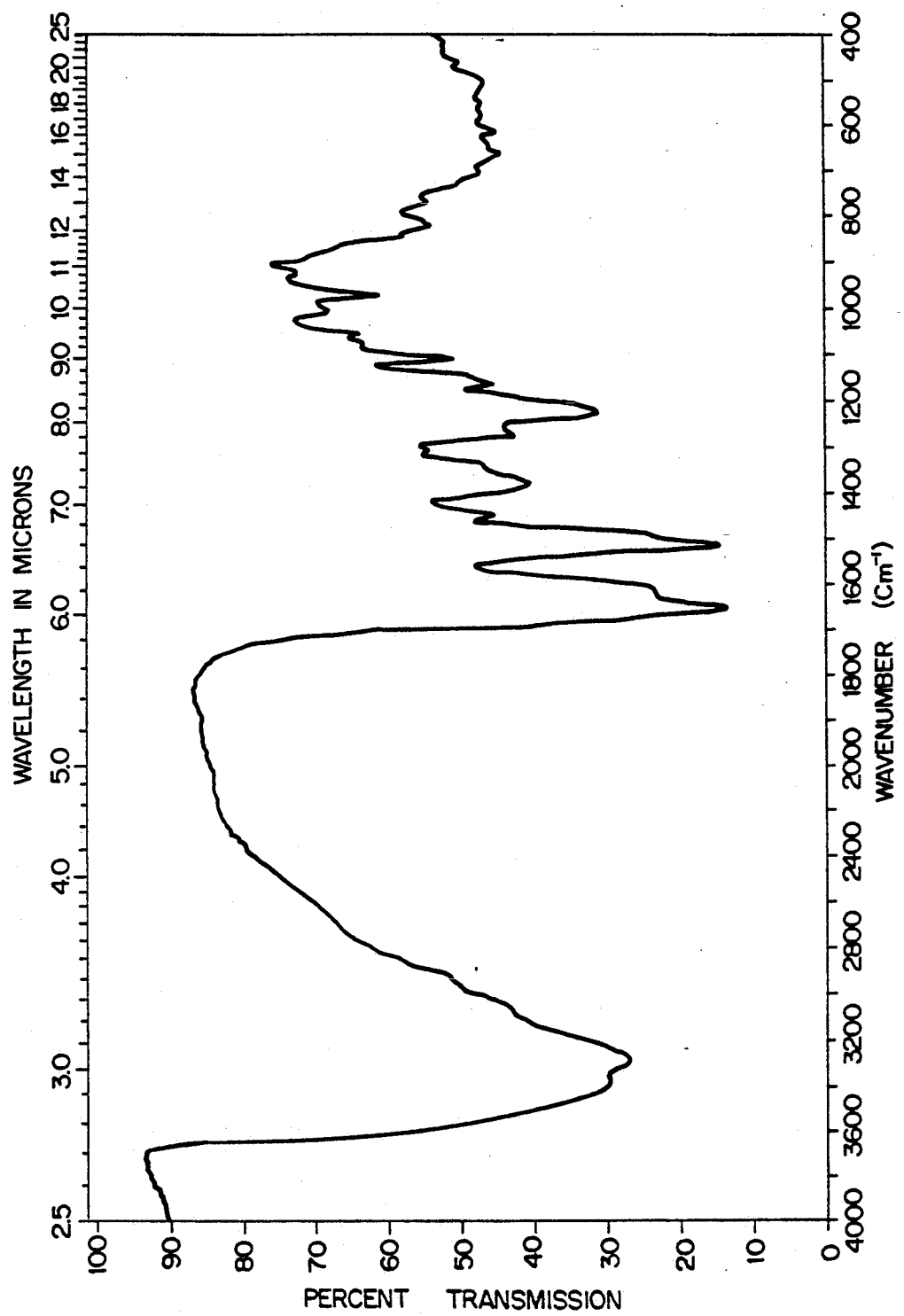
FIG. 2 shows the infrared (IR) absorption spectrum of BU-4344V (KBr, pellet)
Figure 3:
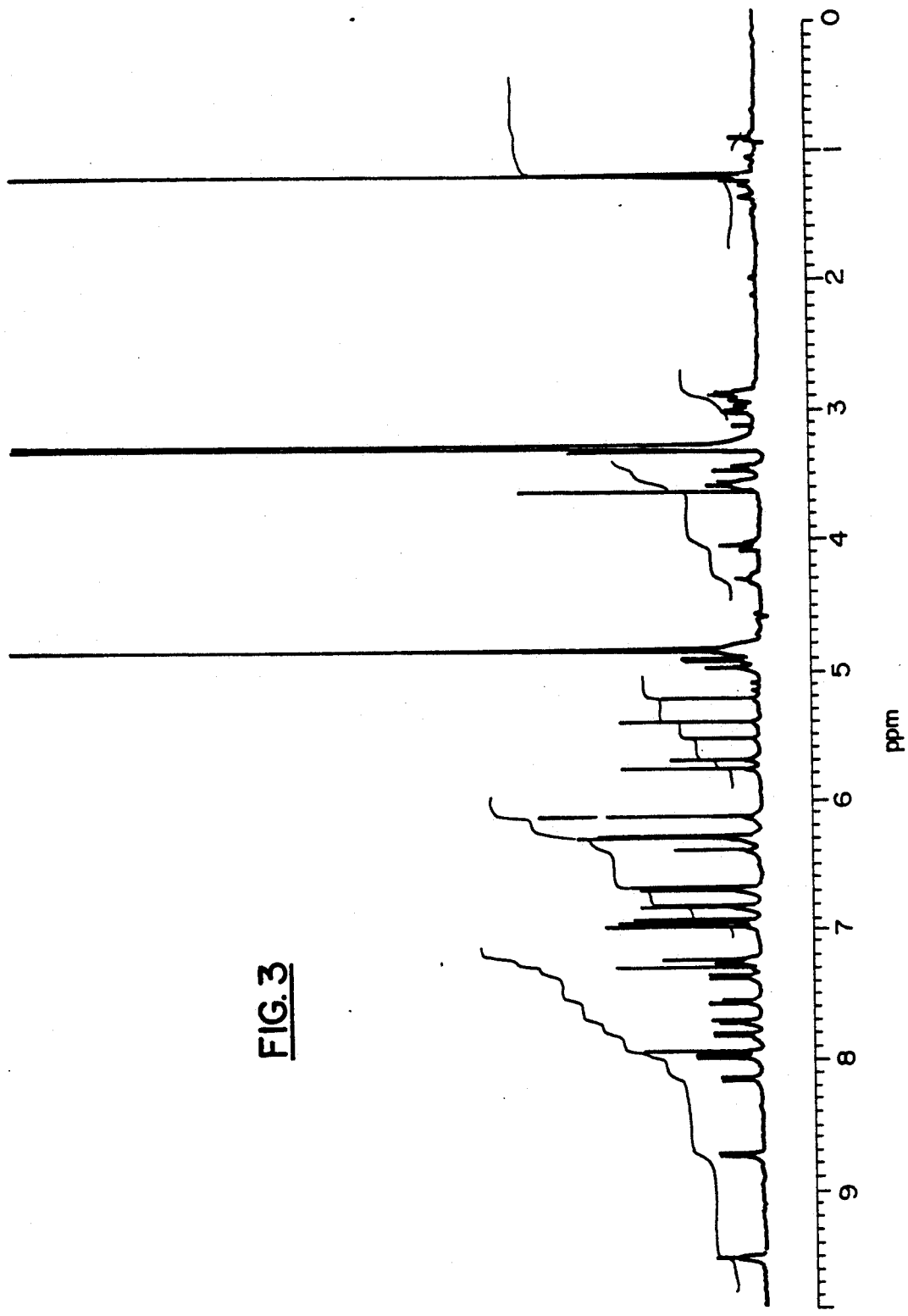
FIG. 3 shows the proton magnetic resonance ($^1$H-NMR) spectrum of BU-4344V in $CD_3OD$ (400 MHz)
Figure 4:
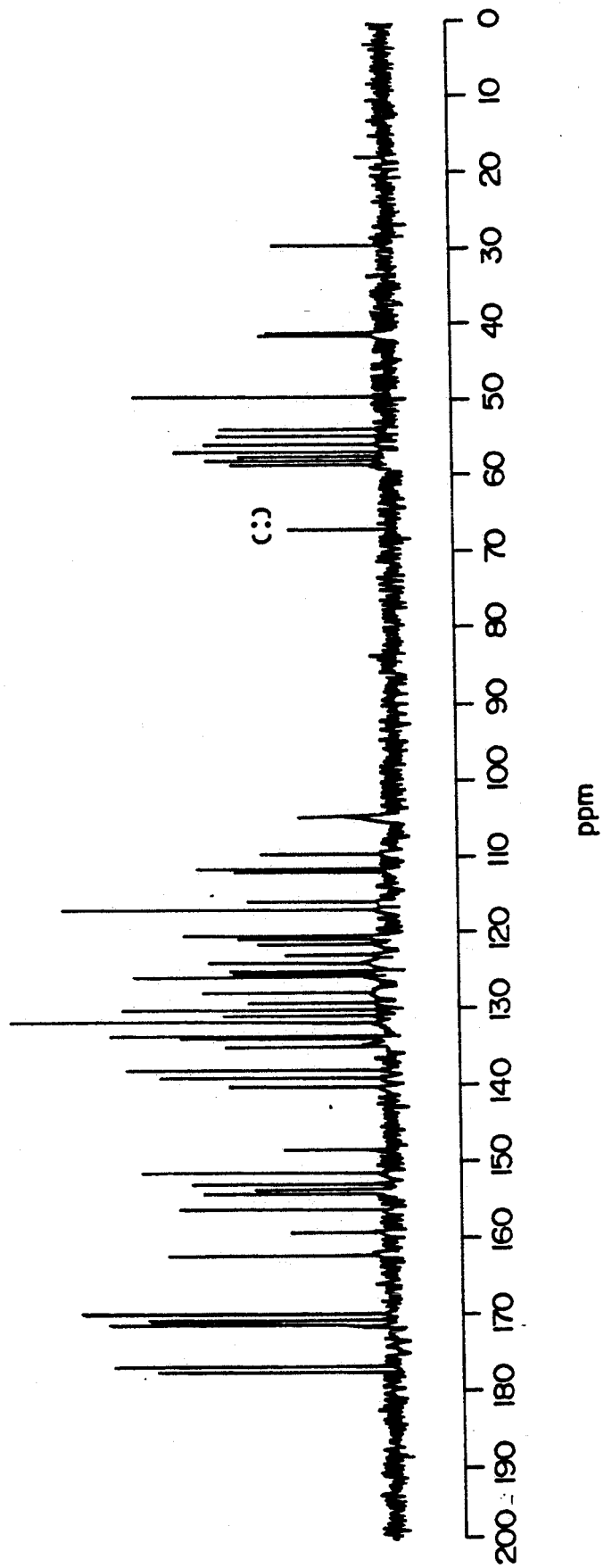
FIG. 4 shows the carbon magnetic resonance ($^{13}$C-NMR) spectrum of BU-4344V in 23% $ND_4OD$ (100 MHz)

The physico-chemical properties of BU-4344V are summarized in Table 5. Elemental analysis was performed after drying in vacuo at 50° C. overnight. The found values were C: 59.28, 59.00; H: 4.56, 4.56; N 9.05, 9.02; Cl: 2.74. The UV spectrum of BU-4344V is shown in FIG. 1 and shows: $UV_{max}^{MeOH}$ nm ($E_{1\ cm}^{1\%}$): 215 (570), 248 (sh, 260), 263 (sh, 192), 285 (126), and 302 (sh, 102). Bathochromic shifts were observed in the spectrum measured in 0.1N NaOH. The IR spectrum of BU-4344V in potassium bromide is shown in FIG. 2. The following peaks are evident 3400 (br), 3300 (br), 1645, 1610, 1510, 1380, and 1225 $cm^{-1}$. The $^1$H-NMR (400 MHz in $CD_3OD$) and $^{13}$C-NMR (100 MHz in 23% $ND_4OD$) spectra are shown in FIGS. 3 and 4, respectively. Their resonance patterns and chemical shifts, combined with the $^1$H-$^1$H COSY experiments, revealed the following partial structures:

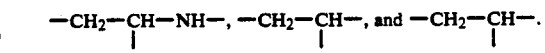

The antiviral antibiotic BU-4344V was hydrolyzed overnight with 6N hydrochloric acid at 105° C. under a nitrogen atmosphere, and the hydrolysate was subjected to amino acid analysis. Tyrosine was detected and was accompanied by a series of other amino acids. These amino acids were also observed by silica gel TLC (phenol /$H_2O$=4:1).

TABLE 5

| Physico-Chemical Properties of BU-4344V | |
| --- | --- |
| Nature | Colorless Needles |
| MP | >300° C. |
| $[\alpha]_D^{27}$ (c 0.5, MeOH) | −13° |
| Microanalysis Found | C: 59.28, 59.00; H: 4.56, 4.56; N: 9.05, 9.02; Cl: 2.74 |
| UV $\lambda_{max}^{MeOH}$ nm ($E_{1\ cm}^{1\%}$) | 215(570), 248(sh, 260), 263 (sh, 192), 285(126), 302(sh, 102); in 0.1N NaOH, 226(360), 237 (368), 293(166) |
| IR ν (KBr) $cm^{-1}$ | 3400, 3300, 1645, 1610, 1510, 1380, 1225 |
| HPLC* Rt. (Min.) | 5.7 |
| TLC** Rf. | 0.58 |

*YMC A-301-3 Yamamura Chem. Lab. Co.; eluant $CH_3CN$/0.15% $KH_2PO_4$, pH 3.5; gradient 0-3 minutes (15/85-40/60), 3-9 minutes (40/60); flow rate 1 ml/minute.
**Merck Kieselgel 60 (n-BuOH:MeOH:$H_2O$ = 4:1:2)

Structure elucidaton by degradative and spectroscopic studies disclosed that the antiviral antibiotic BU-4344V had a unique peptide structure partly related to aglycones of the vancomycin class of antibiotics. The chemical structure of BU-4344V was established as shown in Formula I.

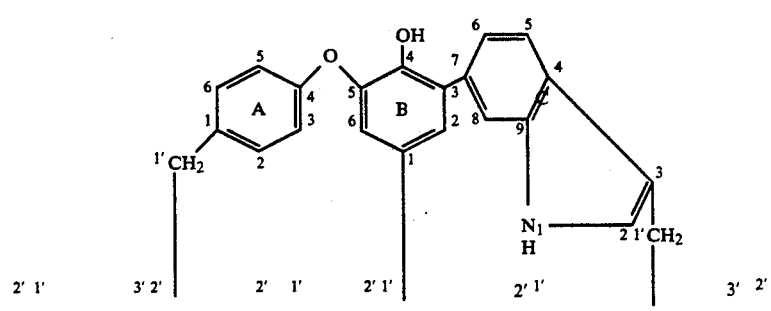

I

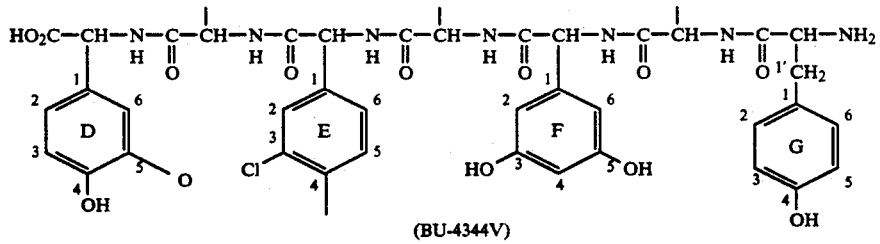

(BU-4344V)

The antivral antibiotic BU-4344V having Formula I showed the quasi-molecular ion peaks at m/z 1,169 and 1,171 by its negative and positive FAB-MS, respectively, which in combination with elemental analysis allowed to assign a molecular formula of $C_{61}H_{51}N_8O_{15}Cl$ to BU-4344V. The $^1$H-NMR and $^{13}$C-NMR spectra, as listed in Table 6, coupled with the $^1$H-$^1$H COSY spectrum, indicated the presence of seven aromatic and seven aliphatic units as shown below.

TABLE 6

$^{13}$C and $^1$H-NMR Spectral Data of BU-4344V (DMSO-d$_6$, 70° C.)

| Group | $^{13}$C | $^1$H(JHz) |
|---|---|---|
| A1 | 134.5 | |
| 2 | 133.0 | 7.59(8.6, 1.0) |
| 3 | 122.4 | 7.40(8.6, 2.4) |
| 4 | 154.2 | |
| 5 | 123.7 | 7.20(8.6, 2.4) |
| 6 | 130.4 | 7.87(8.6, cal) |
| 1' | 40.3 | 2.80(12.0) |
|  |  | 3.43 |
| 2' | 56.6 | 4.55(12.0, 2.0) |
| 3' | 169.4* | |
| NH |  | 8.11(12.0) |
| B1 | 129.6 | |
| 2 | 130.8 | 5.62(2.1) |
| 3 | 131.3 | |
| 4 | 138.5 | |
| 5 | 148.7 | |
| 6 | 107.9 | 5.57(2.1) |
| 1' | 54.5 | 6.19(8.6) |
| 2' | 168.3 | |
| NH |  | 8.66(8.6) |
| C1 |  | 10.48(2.1) |
| 2 | 124.2 | 7.04(2.1) |
| 3 | 110.4 | |
| 4 | 125.5 | |
| 5 | 120.3 | 7.89(9.0) |
| 6 | 121.2 | 6.63(9.0, <1) |
| 7 | 134.4 | |
| 8 | 114.8 | 7.36(<1) |
| 9 | 137.0 | |
| 1' | 29.2 | 2.89(12.8) |
|  |  | 3.40 |
| 2' | 52.4 | 6.10 |
| 3' | 167.4 | |
| NH |  | 9.24(4.0) |
| D1 | 126.6 | |
| 2 | 119.4 | 7.06(8.6, 1.7) |
| 3 | 117.2 | 7.00(8.6) |
| 4 | 147.7 | |
| 5 | 144.7 | |
| 6 | 114.1 | 5.21(1.7) |
| 1' | 54.3 | 5.45(8.1) |
| 2' | 170.3 | |
| NH |  | 9.22(8.1) |
| E1 | 135.2 | |
| 2 | 133.7 | 7.91(1.9) |
| 3 | 128.1 | |
| 4 | 159.1 | |
| 5 | 125.7 | 6.72(8.6) |
| 6 | 128.9 | 7.31(8.6, 1.9) |
| 1' | 53.4 | 4.90(5.1) |
| 2' | 169.9 | |
| NH |  | 9.25(5.1) |
| F1 | 141.0 | |
| 2 | 103.9 | 6.06(2.1) |
| 3 | 157.7 | |
| 4 | 101.2 | 5.81(2.1) |
| 5 | 157.7 | |
| 6 | 103.9 | 6.06(2.1) |
| 1' | 55.7 | 5.08(8.6) |
| 2' | 170.6 | |
| NH |  | 8.33(8.6) |
| G1 | 125.2 | |
| 2 | 129.8 | 6.51(8.3) |
| 3 | 115.2 | 6.26(8.3) |
| 4 | 156.0 | |
| 5 | 115.2 | 6.26(8.3) |
| 6 | 129.8 | 6.51(8.3) |
| 1' | 36.2 | 2.60(13.5) |
|  |  | 3.18 |
| 2' | 54.4 | 4.04(13.5, 3.0) |
| 3' | 169.5* | |

*May be interchangeable.

Acid hydrolysis (6N HCl, 110°, 16h) and/or reductive acid hydrolysis (HI/P, 110° C., 16h) of BU-4344V gave three ninhydrin positive products of Formulas II, III and IV.

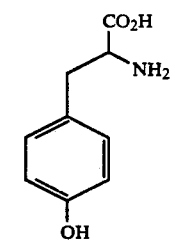

II

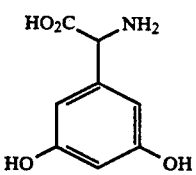

III

Compounds of Formulas II and III were identified as D-tyrosine ($[\alpha]25/D$ +10.0°, C=2.0, 5N HCl, Dawson, R. M. C., et al. (Ed.): Data for Biochemical Research, Second Ed. The University Press, Oxford, 1968; found $[\alpha]_D^{25}$+8.0°, C=0.58, 5N HCl) and 3,5- dihydroxyphenylglycine based on their spectral analysis and pysico-chemical data.

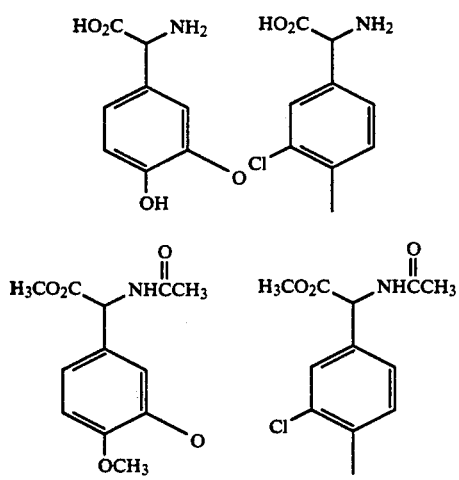

IV

V

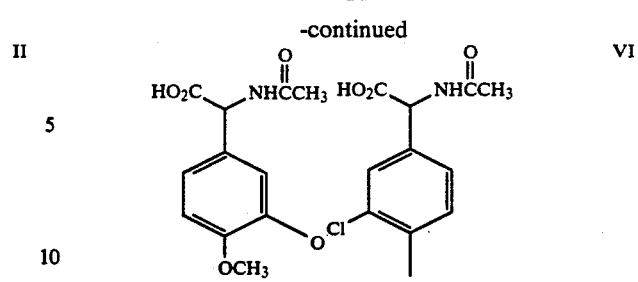

VI

The structure of the compound of Formula IV. was determined to be a biphenylether bis-amino acid by the following experiments. Upon N-acetylation in methanol followed by methylation with diazomethane, the compound of Formula IV gave the di-N-acetyl-tri-O-methyl derivative of Formula V, which showed the molecular ion peak at m/z 492 together with an isotope ion peak at m/z 494 indicating the presence of a chlorine in the molecule. The ether linkage of the two phenyls and the substituents on the rings of Formula IV were assigned based on the calculated $^{13}$C chemical shift values of aromatic carbons and by COLOC experiment ($^2$JC-H and/or $^3$JC-H of the quarternary carbons). The structure was further confirmed by NOESY experiment on the compound of Formula VI which was obtained by mild saponification of the compound of Formula V. Clear NOEs were observed between 4-methoxy protons ($\delta$3.70) and the ortho ($\delta$7.01) and meta ($\delta$7.14) protons.

Analysis of the $^1$H-$^{13}$C COSY and long range $^1$H-$^{13}$C COSY (8 Hz) spectra of BU-4344V established seven partial ring structures, designated as A to G, as shown in the structure of Formula I. It is clear that the hydrolysis products of Formulas II, III and IV originated from units G, F and, D and E, respectively. The presence of an indole ring was supported by positive Ehrlich and ferric chloride-sulfuric acid reactions of BU-4344V. In addition, the direct linkage between B-3 and C-7 carbons was revealed by long range couplings between B-2 proton ($\delta_H$ 5.62) and C-7 carbon ($\delta_c$ 134.4), and C-8 proton ($\delta_H$ 7.36) and B-3 carbon ($\delta_c$ 131.3). The linkages of seven amino acid units were determined by analysis of NOE correlations between protons of these units, especially between $\alpha$-methines and/or amide protons.

The position of tyrosine at the N-terminal was further confirmed by Edman degradation of BU-4344V. After first cycle of degradation, BU-4344V gave PTH-tyrosine together with the hexapeptide. The structure of the aromatic ring system of the upper half of Formula I was confirmed by $^{13}$C chemical shifts comparison with the inhibitor complestatin having Formula VII (Seto, H., et al., *Tetrahedron Letters*, 30, 4987-4990, 1989).

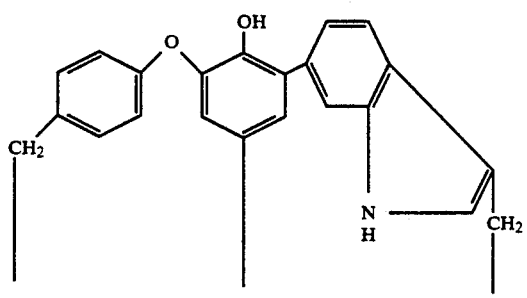

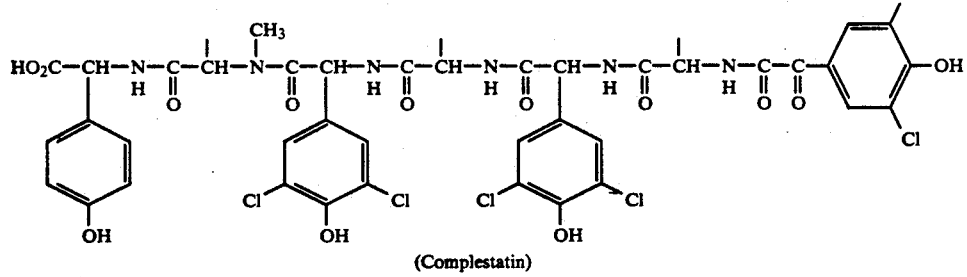

(Complestatin)

The corresponding $^{13}C$ signals of A,B, and C units of BU-4344V and complestatin agreed with each other within the range of 0–3.2 ppm.

The antiviral antibiotic BU-4344V is structurally related to the glycopeptide antibiotics such as vancomycin, ristocetin and teicoplanin, but BU-4344V has no sugar units and possesses the indole nucleus instead of the modified tyrosine or β-hydroxytyrosine unit contained in these well-known antibiotics. The antiviral antibiotic BU-4344V is, however, related to complestatin which was recently isolated as an anti-complement substance (Kaneko, I., et al., *J. Antibiotics*, 42, 236–241, 1989).

The antiviral antibiotic designated BU-4344V has physico-chemical properties which in substantially pure form:

(a) appears as colorless needles;
(b) is soluble in dimethyl sulfoxide, methanol, and alkaline water and is insoluble in dichloromethane, n-hexane, and water;
(c) exhibits a positive response to iodine vapor, sulfuric acid, ferric chloride, and Rydon-Smith reagents, and exhibits a negative response to Dragendorff and anthrone-sulfuric acid reagents on a silica gel thin-layer chromatography plate;
(d) migrates to the anode at pH 8.0 by paper electrophoresis;
(e) has a melting point greater than 300° C.;
(f) has a specific optical rotation $[\alpha]^{27°}$ of $-13°$ (c 0.5, $CH_3OH$);
(g) has an elemental analysis for carbon of 59.28% and 59.00%, for hydrogen of 4.56% and 4.56%, for nitrogen of 9.05% and 9.02%, and for chlorine of 2.74%;
(h) has an apparent molecular formula of $C_{61}H_{51}N_8O_{16}Cl$;
(i) has an ultraviolet absorption spectrum in methanol solution and 0.1N NaOH solution substantially, as shown in FIG. 1;
(j) has an infrared absorption spectrum (KBr) substantially, as shown in FIG. 2;
(k) has a 400 MHz proton magnetic resonance spectrum in $CD_3OD$ substantially, as shown in FIG. 3;
(l) has a 100 MHz carbon-13 magnetic resonance spectrum in 23% $ND_4OD$ substantially, as shown in FIG. 4;
(m) has a retention time of 5.7 minutes in high pressure liquid chromatography using reversed-phase silica gel with $CH_3CN/0.15\%$ $KH_2PO_4$, pH 3.5; and
(n) has an Rf value of 0.58 in thin-layer chromatography using silica gel with n-BuOH-$CH_3OH$-$H_2O$ (4:1:2).

ANTIVIRAL ACTIVITY OF BU-4344V

In vitro antiviral activity of BU-4344V was assessed using the herpes simplex virus type 1 (KOS strain) - Vero cell and influenza virus type A (Victoria strain) - Madin Darby canine kidney (MDCK) cell systems by the dye-uptake assay method [*Antiviral Research*, 3, 223–234 (1986)]. The cell suspension (200 μl), containing $2 \times 10^4$ cells, was inoculated to each well of 96-well microplates and cultured at 37° C. for 48–72 hours under humidified 5% $CO_2$-95% air environment. The growth medium in each well was replaced with 250 μl of fresh medium (Eagle MEM without serum) containing BU-4344V at various doses, and then 50 μl medium containing approximately $10 \times TCID_{50}$ of the viruses was added to each well. For cytotoxicity tests, the same set of wells, without the viruses, were prepared. After 72 hours of incubation, the degree of inhibition of the viral-induced cytopathic effect and the drug-induced cytotoxicity were determined. $ID_{50}$ was expressed as the concentration showing 50% inhibition of the cytopathic effect of control, and $TD_{50}$ was the concentration exhibiting 50% cytotoxicity against Vero or MDCK cells without viral infection. Acyclovir and ribavirin were used as reference compounds of anti-HSV activity and anti-influenza virus activity, respectively. The antiviral activity of BU-4344V was also determined using a conventional plaque reduction assay method.

The results are shown in Tables 7 and 8. BU-4344V demonstrated potent anti-influenza virus activity ($ID_{50}$: 3.6 μg/ml) by the dye-uptake assay, and its antiviral activity was more potent than that of ribavirin. In the plaque-reduction assay, the antiviral activity of BU-4344V showed somewhat weaker activity than that by the dye-uptake assay. BU-4344V exhibited antiviral activity against HSV with $ID_{50}$ values of approximately 40 μg/ml by the dye-uptake assay, but it did not show any anti-HSV activity by the plaque reduction assay.

TABLE 7

| | Activity Against Influenza Virus Type A (MDCK Cells) of BU-4344V | | | |
|---|---|---|---|---|
| | Dye-Uptake Assay | | Plaque-Reduction Assay | |
| | $ID_{50}$ (μg/ml) | $TD_{50}$ (μg/ml) | $ID_{50}$ (μg/ml) | MTD* (μg/ml) |
| BU-4344V | 3.6 | >200 | 66 | >200 |
| Ribavirin | 10 | >100 | 3.8 | >100 |

*MTD: Minimal Toxic Dose

TABLE 8

| | Activity Against Herpes Simplex Virus Type I (Vero Cells) of BU-4344V | | | |
|---|---|---|---|---|
| | Dye-Uptake Assay | | Plaque-Reduction Assay | |
| | $ID_{50}$ (μg/ml) | $TD_{50}$ (μg/ml) | $ID_{50}$ (μg/ml) | MTD* (μg/ml) |
| BU-4344V | 44 | >200 | >25 | 25 |

TABLE 8-continued

| Activity Against Herpes Simplex Virus Type I (Vero Cells) of BU-4344V | | | |
|---|---|---|---|
| Dye-Uptake Assay | | Plaque-Reduction Assay | |
| $ID_{50}$ (μg/ml) | $TD_{50}$ (μg/ml) | $ID_{50}$ (μg/ml) | MTD* (μg/ml) |
| Acyclovir 0.2 | >100 | 0.25 | >100 |

*MTD: Minimal Toxic Dose

ANTIBIOTIC ACTIVITY OF BU-4344V

The in vitro antibacterial activity of BU-4344V was determined by the two-fold agar dilution method using a Steer's multi-inoculating apparatus. As shown in Table 9, BU-4344V exhibited fairly good inhibitory activity against various staphylococcal bacteria.

TABLE 9

| Antibacterial Activity of BU-4344V | |
|---|---|
| Test Organisms | MIC (mcg/ml) |
| *Staphylococcus aureus* 209P | 12.5 |
| *Staphylococcus aureus* Smith | 12.5 |
| *Staphylococcus aureus* D136 | 25.0 |
| *Staphylococcus aureus* #52-34 | 12.5 |
| *Staphylococcus aureus* A20239 | 25.0 |
| *Staphylococcus aureus* A9606 | 12.5 |
| *Staphylococcus aureus* A15097 | 12.5 |
| *Staphylococcus epidermidis* D153 | 6.3 |
| *Staphylococcus epidermidis* A22152 | 25.0 |
| *Enterococcus faecalis* A9612 | 50.0 |
| *Micrococcus luteus* PCI1001 | 1.6 |
| *Bacillus subtilis* PCI219 | 6.3 |
| *Escherichia coli* Juhl | >100.0 |

METHODS OF USE AND PHARMACEUTICAL COMPOSITIONS

The antiviral antibiotic BU-4344V, according to the present invention and pharmaceutical compositions thereof, are useful to inhibit the growth of Gram-positive bacteria and of viruses, especially the influenza virus. The antibacterial and antiviral effects of BU-4344V was demonstrated as described above.

In general, BU-4344V may be administered orally or parenterally in its pure-solid form, in dilute solution or suspension or in a concentrate and prepared for unit dose or multi-dose presentation. When administered parenterally, by intravenous or intramuscular or subcutaneous injection, or when administered orally, the dosage administered will be dependent on the age and weight of the mammalian species being treated, the route of administration, and the type and severity of the infectious condition being treated and other factors readily evaluated by the physician or veterinarian in attendance.

In respect to pharmaceutical compositions containing the antibiotic herein, carrier and other ingredients should be such as not to diminish the therapeutic effects of the antibiotic. Suitable dosage forms for oral use are tablets, dispersible powders, granules, capsules, syrups, and elixirs. Examples of parenteral forms are solutions, suspensions, dispersions, emulsions, and the like. The compositions for oral use may contain one or more conventional adjuvants, such as sweetening agents, flavoring agents, coloring agents, and preserving agents, in order to provide a composition of suitable pharmaceutical elegance. Tablets may contain the active ingredient in admixture with conventional pharmaceutically acceptable excipients, including inert diluents such as calcium carbonate, sodium carbonate, lactose, and talc; granulating and disintegrating agents such as starch and alginic acid; binding agents such as starch, gelatin, and acacia; and lubricating agents such as magnesium stearate, stearic acid, and talc. The tablets may be uncoated or coated by known techniques to delay disintegration and absorption in the gastrointestinal tract and thereby provide a sustained action over a longer period. Similarly, suspensions, syrups, and elixirs may contain the active ingredient in admixture with any of the conventional excipients utilized for the preparation of such compositions, such as suspending agents (e.g., methylcellulose, tragacanth, and sodium alginate), wetting agents (e.g., lecithin, polyoxyethylene stearate), and preservatives, such as ethyl p-hydroxybenzoate. Capsules may contain the active ingredient alone or admixed with an inert solid diluent, such as calcium carbonate, calcium phosphate, and kaolin. The injectable compositions are formulated as shown in the art and may contain appropriate dispersing or wetting agents and suspending agents identical or similar to those mentioned above.

The daily dosage for adult human treatment will preferably range from about 100 mg to about 1,000 mg of the active BU-4344V for a 70 kg adult, depending on the nature of the infection and the frequency and route of administration inter alia. It will be appreciated that in some instances, e.g., in the treatment of neonates, infants, and juveniles, smaller dosages than adult dosages may be desired.

The pharmaceutical compositions of this invention, thus, will generally comprise a growth inhibitory amount (i.e., an amount effective to inhibit the growth of the virus causing the condition of infection to be treated) of BU-4344V in a suitable pharmaceutical acceptable carrier, such as water or alcohols which may contain fillers, stabilizers, wetting agents, emulsifying agents, and dispersing agents, to name but a few conventional carriers, adjuvants, and excipients which may be employed.

The following example is given by way of illustration only and is not to be construed to limit the scope of the invention. Many apparent variations are possible without departing from the spirit and scope of the invention.

EXAMPLE 1

Fermentation of BU-4344V

A mature agar slant of Actinomadura carvasata subsp. kistnae Strain No. S382-8 (ATCC No. 55076) was used to inoculate a 500-ml Erlenmeyer flask containing 100 ml of the vegetative medium comprising soluble starch (Nichiden Kagaku) 0.5%, glucose 0.5%, fish meat extract (Mikuni Kagaku) 0.1%, yeast extract (Oriental Yeast) 0.1%, NZ-case (Sheffield) 0.2%, NaCl 0.2%, and $CaCO_3$ 0.1%. The pH was adjusted to 7.0 before sterilization.

The culture was incubated at 32° C. for 4 days on a rotary shaker (200 rpm), and 5 ml of the growth was transferred to a 500-ml Erlenmeyer flask containing 100 ml of the production medium comprising glucose 2%, fish meal D30X ® (Banyu Eiyo Company) 1%, and $CaCO_3$ 0.5% (pH 7.0 prior to autoclaving). The fermentation was carried out at 28° C. for 7 days on a rotary shaker (200 rpm) The antibiotic production in the fermentation broth was monitored by the conventional dye-uptake assay method using influenza virus Type A. The fermentation broth showed the antiviral activity at 48 times dilution through 4 to 7 days. A scaled-up fermentation was also carried out using stir-jar fermentors.

A 500-ml portion of the seed prepared by the flask fermentation was used to inoculate a 20-liter stir-jar fermentor containing 12 liters of the production medium. The fermentation was carried out at 28° C. for 5 days (113 hours) with stirring at 250 rpm and an aeration rate of 12 liters per minute. The activity of the fermentation broth was almost the same as in the case of flask fermentation.

Extraction and Purification of BU-4344V

The fermentation broth (9.6 L) was extracted with n-butanol (5.5 L) under stirring for 1 hour. The extract was concentrated to dryness to give a brown oil (7.0 g), which was triturated with water (200 ml). The oil was extracted with ethyl acetate (200 ml) and n-butanol (200 ml), successively. The activity was found in the n-butanol extract, which was evaporated to dryness to give a reddish powder (2.57 g). The powder was dissolved in methanol and subjected to Sephadex LH-20 (1.8 L) column chromatography with methanol. After washing with 900 ml of methanol, the eluate was collected in 10 g-fractions and monitored by HPLC (YMC A-301-3 Yamamura Chem. Lab. Co.; eluant CH3CN/0.15% KH2PO4, pH 3.5; gradient 0-3 minutes (15/85-40/60), 3-9 minutes (40/60); flow rate 1 ml/minute; detection UV at 254 nm; retention time 5.7 minutes). Evaporation of the collected fractions (Nos. 36-63) yielded a pale yellow amorphous powder (835 mg). The powder was dissolved in aqueous methanol (30 ml) and charged on a column of reversed-phase silica gel [500 ml, silica gel corresponding to the content of a PrepPAK-500/C18 cartridge column (Waters)].

The column was developed with 30% (650 ml), 40% (750 ml), 60% (800 ml), and 80% (1 L) aqueous methanol, and finally with methanol (1.5 L). The desired compound was found in the 40%-100% methanol eluates, which were combined and evaporated to give 588 mg of a light yellow powder. The semi-pure sample (580 mg) was purified by silica gel (Merck Kieselgel 60, 300 ml) column chromatography with 20% methanol-dichloromethane (1.8 L) and 50% methanol-dichloromethane (1.5 L), successively. The pure sample (409 mg) was isolated from the 50% methanol-dichloromethane eluate. Crystallization of a sample (100 mg) from methanol afforded colorless needles of the antiviral antibiotic BU-4344V (30 mg).

What is claimed is

1. A biologically pure culture of the microorganism *Actinomadura parvosata* subsp. kistnae ATCC No. 55076, which is capable of producing the antiviral antibiotic BU-4344V in a recoverable quantity upon cultivation in a culture medium containing assimilable sources of carbon and nitrogen under submerged aerobic conditions.

2. The process for the preparation of BU-4344V having the formula

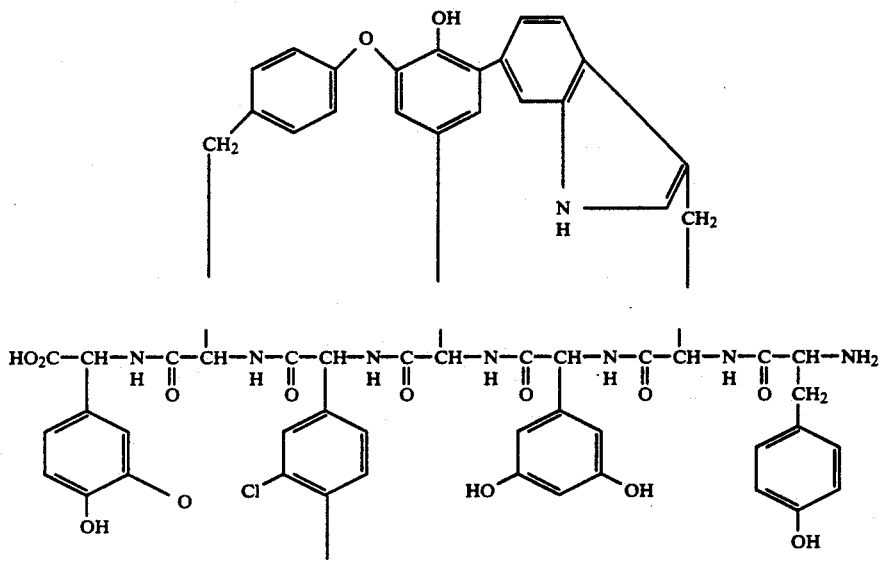

which comprises cultivating a BU-4344V-producing strain of *Actinomadura parvosata* subsp. kistnae having the identifying characteristics of ATCC No. 55076, or a mutant thereof, in culture medium containing assimilable sources of carbon and nitrogen under submerged aerobic conditions until a substantial amount of BU-4344V is produced by said organism in said culture medium and then recovering BU-4344V from the culture medium.

* * * * *